US006954545B2

(12) United States Patent
Welch et al.

(10) Patent No.: US 6,954,545 B2
(45) Date of Patent: Oct. 11, 2005

(54) USE OF A SCANNER TO DETERMINE THE OPTICAL DENSITY OF CALCINED COKE AS A MEASURE OF COKE QUALITY

(75) Inventors: Gary E. Welch, Ponca City, OK (US); Hooshang Jozavi, Ponca City, OK (US)

(73) Assignee: Conocophillips Company, Houston, TX (US)

( * ) Notice: Subject to any disclaimer, the term of this patent is extended or adjusted under 35 U.S.C. 154(b) by 755 days.

(21) Appl. No.: 09/934,946

(22) Filed: Aug. 22, 2001

(65) Prior Publication Data

US 2002/0012448 A1 Jan. 31, 2002

Related U.S. Application Data

(63) Continuation-in-part of application No. 09/258,859, filed on Feb. 26, 1999, now Pat. No. 6,330,343.

(51) Int. Cl.[7] .............................................. G06K 9/00
(52) U.S. Cl. ........................................................ 382/108
(58) Field of Search ................................ 382/100, 108, 382/109, 141, 286; 348/92, 128, 135, 180; 396/34, 124, 237.1, 237.2, 928; 707/2, 42, 81, 127, 136, 190, 191; 374/5, 19, 55, 56, 57, 187; 208/401, 402

(56) References Cited

U.S. PATENT DOCUMENTS

| | | | | |
|---|---|---|---|---|
| 4,617,682 A | | 10/1986 | Mori et al. ................. 382/108 |
| 4,641,036 A | * | 2/1987 | Ohno et al. ................. 250/574 |
| 5,132,791 A | | 7/1992 | Wertz et al. ................... 348/88 |
| 5,432,595 A | | 7/1995 | Pechersky ................... 356/35.5 |
| 5,440,648 A | | 8/1995 | Roberts et al. ............. 382/141 |
| 5,443,164 A | | 8/1995 | Walsh et al. ................. 209/580 |
| 5,828,500 A | | 10/1998 | Kida et al. ................... 359/798 |
| 5,841,882 A | * | 11/1998 | Celeski ....................... 382/109 |

OTHER PUBLICATIONS

Carbon vol. 34, No. 3, pp. 375–385, 1996, Elsevier Science Ltd "An Automatic Image Analysis of Coke Texture" By Eilertsen et al.*
"Evaluation of Needle Coke Appearance By Illumination By Reflected Light," Koa Poster at 1997 Carbon Conference, K. Matsuoka, et al., Needle Coke Quality Control and Research Laboratory Section, Marifu Refinery KOA Oil Co., Ltd.
KOA Pre–Prints to 1997 Carbon Conference; "Carbon '97," 23rd Biennial Conference on Carbon Jul. 18–23, 1997; Extended Abstracts and Program, vol. II—Carbonization / Industrial / Carbon Growth / Fibers, The American Carbon Society and Penn State, "Evaluation of Needle Coke Appearance by Illumination by Reflected Light," pp. 238–239.
"Digital Image Analysis: Basic Principals and Industrial Research Applications," by Paige Johnson of Conoco Inc., presented at the OSU College of Osteopathic Medicine, Feb. 26, 1998.

* cited by examiner

Primary Examiner—Andrew W. Johns
Assistant Examiner—Shervin Nakhjavan

(57) ABSTRACT

An improved test for quantifying luster of petroleum products in particle form, especially coke, as an index of quality. A representative sample of the product is obtained and prepared. A digital image of the sample is formed using a scanner. The image is then processed digitally to produce a representative luster or optical density measurement for the sample. The preceding process may be repeated several times for each sample and the resultant luster or optical density measurements for each iteration are totaled and averaged. Once the luster measurement or optical density for the sample is obtained, it is compared to established parameters to assign a CTE value to the sample, assuming there is sufficient historical data correlating the two measurements. Various refining operating parameters including feedstocks, temperatures and pressures, may be altered to obtain a desired product.

9 Claims, 5 Drawing Sheets

USE OF A SCANNER TO DETERMINE THE OPTICAL DENSITY OF CALCINED COKE AS A MEASURE OF COKE QUALITY

CROSS REFERENCE TO RELATED APPLICATION

This application is a continuation-in-part patent application of U.S. patent application Ser. No. 09/258,859 filed Feb. 26, 1999 now Pat. No. 6,330,343 entitled "A Method for Measuring Coke Quality by Digital Quantification of High Intensity Reflectivity".

BACKGROUND OF THE INVENTION

1. Field of the Invention

The present invention relates generally to an improved method of analyzing petroleum products in particle form. More particularly, the present invention relates to an improved method for analyzing the quality of petroleum by-products in particle form, especially coke, and relates to improved methods for refining petroleum to obtain desirable coke by-products.

2. Prior Art

As will be appreciated by those skilled in the art, petroleum products are analyzed for many purposes by using various tests. The test results are used for many purposes, sometimes even including controlling the refining of these products in order to achieve desired results but more often for appropriately classifying the products for subsequent sale.

For example, coke is a resulting by-product from petroleum refining that must be appropriately classified prior to sale. Cokes are typically classified by measuring their coefficient of thermal expansion (CTE) which provides the rate of expansion (or contraction) of a substance with temperature change.

In one use, coke is used in manufacture of large graphite electrodes for electric arc furnaces employed in the steel industry. It is known that cokes with lower CTE (e.g. FCTE=0.0–2.0×10$^{-7}$/° C.) result in better performance of graphite electrodes under electric arc furnace (EAF) operations than those with higher CTE (e.g. FCTE>4.0×10$^{-7}$/° C.). Therefore, lower CTE cokes are more desirable than higher CTE cokes.

It is believed that, in typical representative coke samples, the lower CTE materials consist of a larger number (percent) of highly needle-like particles than the higher CTE materials. Needle-like particles are those whose structure has a preferential orientation. They are generally elongated as a result; hence the term "needle". For a particular premium coke grade, the needle-like structure is not constant throughout the coke particles of that grade. Instead, there is a distribution of highly needle-like to highly non-needle-like particles.

One known method of classifying coke involves testing or examining these calcined cokes to determine the coke CTE. This procedure involves extrusion of a mixture of calcined coke particles and a binder pitch followed by baking, graphitizing and measurement of CTE of the resulting artifacts. Typically, the artifact is heated and measurements are taken at various temperatures to determine the CTE for a particular batch of coke. As will be appreciated by those skilled in the art, this procedure is fairly involved and time-consuming, on the magnitude of three to four days for a CTE measurement.

The resulting CTE determination has been previously used to segregate cokes into quality grades. However, the known methods for measuring coke CTE are complex and time-consuming. Thus, an improved method for classifying cokes is desirable.

It has been observed that, to even an untrained eye, higher quality cokes are shinier than lower quality ones. Subsequent research has shown (KOA Oil Company, 1997 Carbon Conference, PSU) that there is a correlation between CTE measurements and the "shininess" of a field of coke particles.

Another method of classifying coke is to use the varying reflectivities of the coke. The lustre method of the present invention quantifies this visual perception by digitally measuring the reflection of light from a pan of coke particles. This measurement is the coke's lustre (hereinafter, the phrase "coke lustre" will be used to refer to the intensity of visible light reflected from the surface of a coke particle or a layer of coke particles). The measurement of coke lustre is approximately analogous to extracting and counting the particles with the most needle-like character. Thus, coke lustre reveals information that can be used for ranking cokes based on their needle-like structure that is similar to CTE measuring methods.

Measuring coke lustre is easier than other known methods of physically measuring coke CTE. Classification of cokes based on lustre measurements has been difficult because only small differences in lustre are seen, even when CTE differences are significant. In other words, it has been difficult to correlate the small deviations noticed between coke lustres with a meaningful correlation with CTE variances.

Therefore, a need exists in the art for an improved method of classifying coke. A particularly desirable improvement would be an improved method of classifying coke based on its reflectivity or lustre as opposed to existing methods of physically measuring coke CTE. An even more desirable improvement would be a method for increasing the accuracy and reliability of such a lustre classification method.

SUMMARY OF THE INVENTION

The present invention addresses the above referenced needs in the art. In an exemplary embodiment, the invention provides a method for measuring coke quality by digital quantification of high intensity reflectivity. The invention includes an improved test for qualifying petroleum products, especially coke. The test involves obtaining a sample from a petroleum product (i.e. calcined coke) produced under known operating parameters during petroleum refining. The test enables the user to quickly and efficiently classify the product.

The test generally includes several broad steps. The first step is to obtain a representative sample for the target product, in the exemplary process coke, although the test may work well for other types of petroleum products as well.

The representative sample is then prepared in accordance with standard laboratory protocols (i.e. sieving, de-oiling, etc.) until the sample is properly suited for further testing. The properly prepared sample is then appropriately placed beneath an illuminating device in a manner that promotes the formation of a substantially smooth upper surface. This may require physical leveling of the sample or the like. The critical consideration is that the upper surface of samples being tested are prepared in a uniform manner to remove or at least curtail errant deviations from the test procedure.

The sample is then exposed to illumination. Preferably, a ring light or other lighting mechanism is deployed to shine on the sample with visible light from a desired direction (i.e.

directly over the top surface of the sample). The illumination produces a visible light pattern from the light reflected from the sample's upper surface. As discussed previously, the reflectivity or lustre of a particular sample due to the illumination varies in correlation to the sample's CTE.

The pattern resulting from the illumination is then acquired to capture a digital image of the reflection of the sample. In a preferred embodiment, the digital image was acquired through use of a photography camera. In some circumstances, it may be desirable to slightly magnify the sample for acquisition, but this is not always necessary. Of course, the magnification can be accomplished with lenses or in other conventional manners.

Preferably, the pattern is acquired multiple times to develop an average image to reduce noise. In practice, the pattern was acquired 16 times consecutively although the multitude of acquisitions can be increased or diminished as desired.

Once a representative image has been obtained, it is processed digitally. The digital image is then quantified by measuring the gray levels present in the image. The highest gray levels are extracted and measured to produce a representative lustre measurement for the sample. During this extraction and measurement, a computer is preferably used to select the highest gray levels although specialized equipment having pattern recognition digital processing functions capable of producing and defining the video image as having a low or high CTE may be alternatively employed.

Ideally, the preceding process is repeated several times for each sample and the resultant lustre measurements for each iteration are totaled and averaged to avoid potential errors or deviations. In this manner, a more accurate representative lustre measurement is obtained.

Once the lustre measurement for the sample is obtained, it can be easily related to the CTE of the sample given sufficient historical correlation between the types of measurements.

In order to obtain a desired product (coke with a desired CTE), the various operating parameters of the refining process may be varied until the desired product is obtained. Changes to the operating parameters necessarily alter the lustre (and CTE of the coke), which can then be subsequently remeasured and compared to a desired value. The user may continue to alter the operating parameters until a desirable coke product is obtained as indicated by the resulting lustre or CTE value.

Thus, a principal object of the present invention is to provide an improved method of testing petroleum products for classification.

A basic object of the present invention is to provide a method for varying operating parameters in a petroleum refining process to produce a desirable product.

A related object of the present invention is to increase the efficiency of petroleum processing by providing an improved test that enables users to more quickly classify products.

Another object of the present invention is to provide an improved test that enables users to accurately classify coke products using lustre.

Another object of the present invention is to provide an improved test that increases the reliability of petroleum product classification.

A further basic object of the present invention is to provide more efficient refining of petroleum products.

Another basic object of the present invention is to provide an improved test that reliably measures coke lustre which is closely related to coke coefficient of thermal expansion (CTE).

Figure 6:
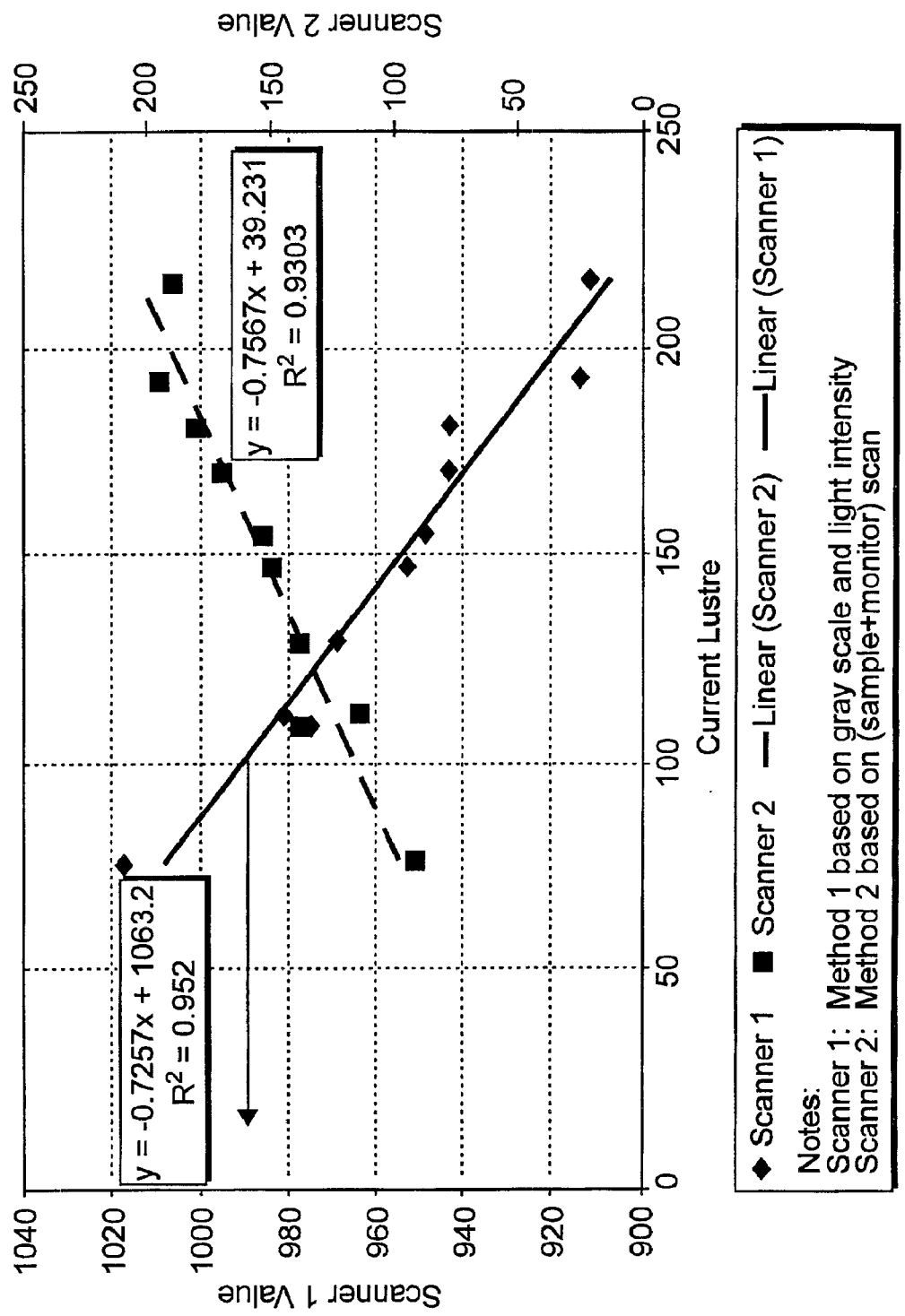
FIG. 6 is a graph charting correlations between existing lustre method data and those obtained by the alternative scanner method.

TABLE 1 is a table depicting comparison of CTEs and lustre measurement variabilities;

TABLE 2 is a table of current lustre method data and those with the alternative scanner method used to plot FIG. 6.

DETAILED DESCRIPTION OF THE PREFERRED EMBODIMENTS

Figure 3:
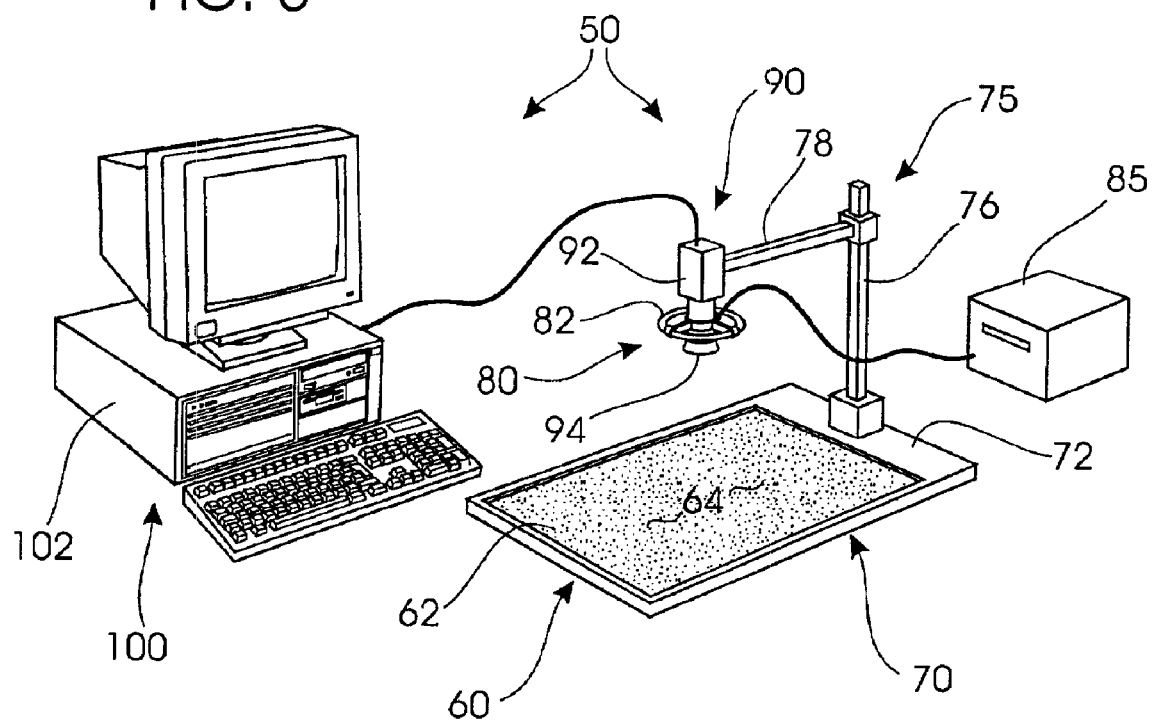
FIG. 3 is a schematic representation of an exemplary embodiment in accordance with the present invention.
Figure 4:
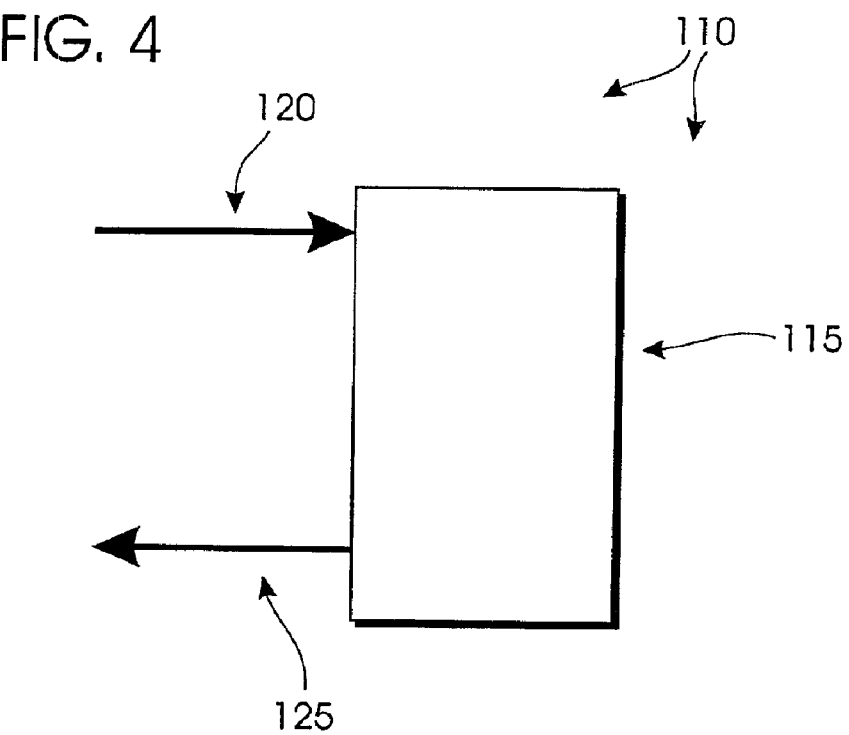
FIG. 4 is a block diagram of the coking portion of a petroleum refining process in accordance with the present invention.

The present invention provides a method for measuring quality of petroleum products in particle form by digital quantification of high intensity reflectivity. Referring initially to FIGS. 3 and 4, in an exemplary embodiment, the invention includes an improved test using a system 50 (FIG. 3) for determination of quality of petroleum cokes. Heretofore, cokes have typically been classified by quantifying coefficient of thermal expansion (CTE). The test involves obtaining a sample 60 from a petroleum product (i.e. coke) produced under known operating parameters during petroleum refining 110 (FIG. 4). The test 50 enables the user to quickly and efficiently classify the product.

The test generally includes several broad steps. The first step is to obtain a representative sample 60 for the target product, generally coke, although the test may work well for other types of petroleum products as well.

The representative sample 60 is then prepared in accordance with standard laboratory protocols (i.e. sieving, de-oiling, etc.) until the sample 60 is properly suited for further testing. The properly prepared sample 62 is then appropriately placed in a tray 70 or similar container.

The tray 70 facilitates the formation of a smooth upper surface 64 in sample 62. The surface 64 may require additional physical leveling of the sample 62 or the like to attain a sufficiently flat surface. The critical consideration is that the upper surface 64 of various samples be prepared in an uniform manner to remove or at least curtail errant deviations from the test 50. The tray 70 may also include a stand 75 selectively offset from the tray floor 72 by a support rod 76. The rod 76 protrudes upwardly from the floor 72 and supports an elongated holder 78. The holder 78 may mount a lighting device 80 and an analog or digital imager 90, but need not necessarily do so.

In a preferred embodiment, the tray 70 and sample 60 are disposed beneath a lighting device 80 and a digital camera 90. The lighting device 80 may comprise a ring light 82 or similar device controlled by power supply 85. Ideally, power supply 85 ensures an invariant power source for the lighting device 80 to prevent deviations in test apparatus 50. The tray 70 and particularly surface 64 are ideally centered directly beneath light 82 and imager 90.

Once properly positioned, the sample 62 is then exposed to illumination by activating the light 82. Preferably, the ring light 82 or other lighting mechanism is deployed to shine on the sample 62 and more particularly the surface 64 with visible light from a desired direction (i.e. directly over the top surface of the sample). This illumination produces a visible light pattern from the light either reflected or emitted from the sample's upper surface 64. As discussed previously, the reflectivity or lustre of a particular sample due to the illumination has been found to be in correlation to the sample's CTE.

The pattern resulting from the illumination is then acquired by the imager 90. Imager 90 may be an analog or digital camera 92 or other similar, conventional device that can capture an image of the reflection of the sample. Preferably, the pattern is acquired multiple times to develop an average image to reduce potential errors.

In some circumstances, it may be desirable to slightly magnify (in the order of 05× to 10×) the sample, but this is not always necessary. Magnification can be accomplished with lens 94 or in any other conventional manner.

Once a representative image has been obtained, it is transmitted to an associated digital processor 100. The processor may include image analysis software and a frame grabber board which converts an analog signal to a digital signal. If a digital camera is used, a frame-grabber is not necessary because the signal is already digital. A bit map of the image is produced which has X and Y coordinates and a gray level for each point, or pixel, in the image. The digital video image is then quantified by measuring the gray levels present in the image. The gray levels are measured from 0 being the blackest to 255 being the whitest. The data is stored as a set of numbers. The highest gray levels are extracted to produce a representative lustre measurement for the sample. In the present case, the gray levels over a certain threshold number are selected and extracted. During this extraction and filtration, a personal computer 102 having a central processing unit is preferably used to select the highest gray levels although specialized equipment having pattern recognition digital processing functions capable of producing and defining the video image as having a low or high lustre may be alternatively employed.

Ideally, the preceding process is repeated several times for each sample and the resultant lustre measurements for each iteration are totaled and averaged to avoid potential errors or deviations. In this manner, a more accurate representative lustre measurement is obtained. Once the lustre measurement for the sample is obtained, it can be easily related to the CTE of the sample given sufficient historical correlation between the two measurements.

The process for production of coke broadly involves the thermal decomposition of heavy liquid hydrocarbons to produce gas, liquid and coke. Those salable products are produced by fractionation and separation by boiling ranges in the refining process. In order to obtain a desired product (coke) with a desired CTE, it becomes a matter of varying the various operating parameters (represented by box 115) of the refining process 110 until the desired product (represented by output line 125) is obtained (FIG. 4). Changes to the operating parameters can include changing feedstocks, changing operational temperatures, changing operational pressures and the like (represented by input line 120). These changes necessarily alter the coke composition and affect the lustre (and CTE of the coke), which can then be subsequently remeasured and compared to a desired value. The operating parameters continue being altered until a desirable coke product is obtained as indicated by the resulting lustre value.

The coke lustre measurements of the present invention can also help in blending various grades of coke with different quality as determined by their CTEs to result in a blended coke with desirable lustre or desirable CTE properties. For example, if various quality cokes have different lustre, a mixture may be blended to obtain a blended coke with a desirable level of net composite lustre.

EXAMPLE 1

Lustre testing as described hereinabove was performed in accordance with an exemplary embodiment of the invention (FIGS. 1–4 and Table 1). The lustre test results are the average of five separate measurements on the same coke sample. As described hereinafter, for the lustre test measurements, about 400–500 grams of de-oiled and crushed (28/100 ty— Tyler standard screen scale fractions are used).

Figure 1:
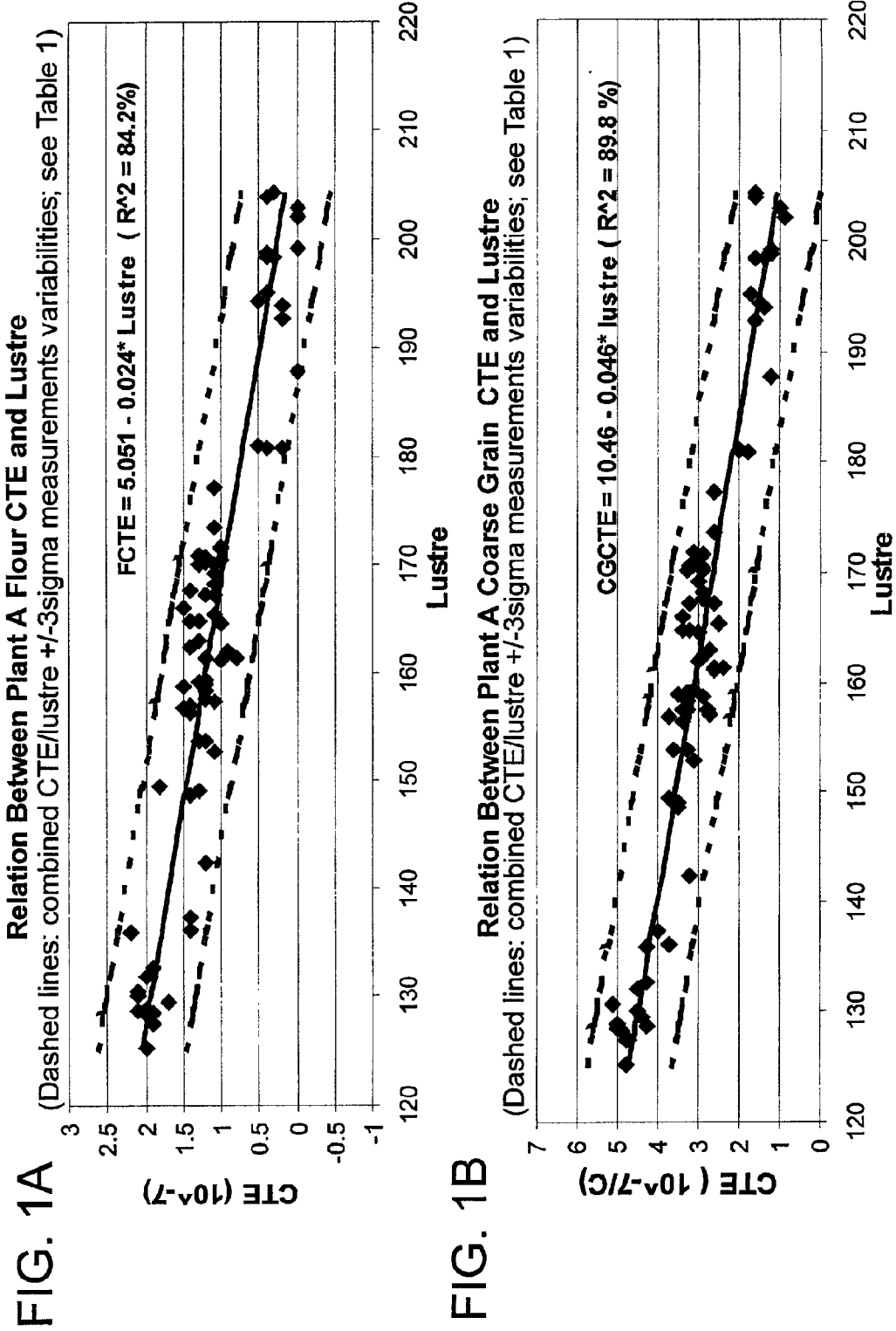
FIG. 1a is a graph depicting relation between samples of Plant A cokes CTE and lustre.
FIG. 1b is a graph depicting relation between Plant A cokes coarse grain CTE and lustre.
Figure 2:
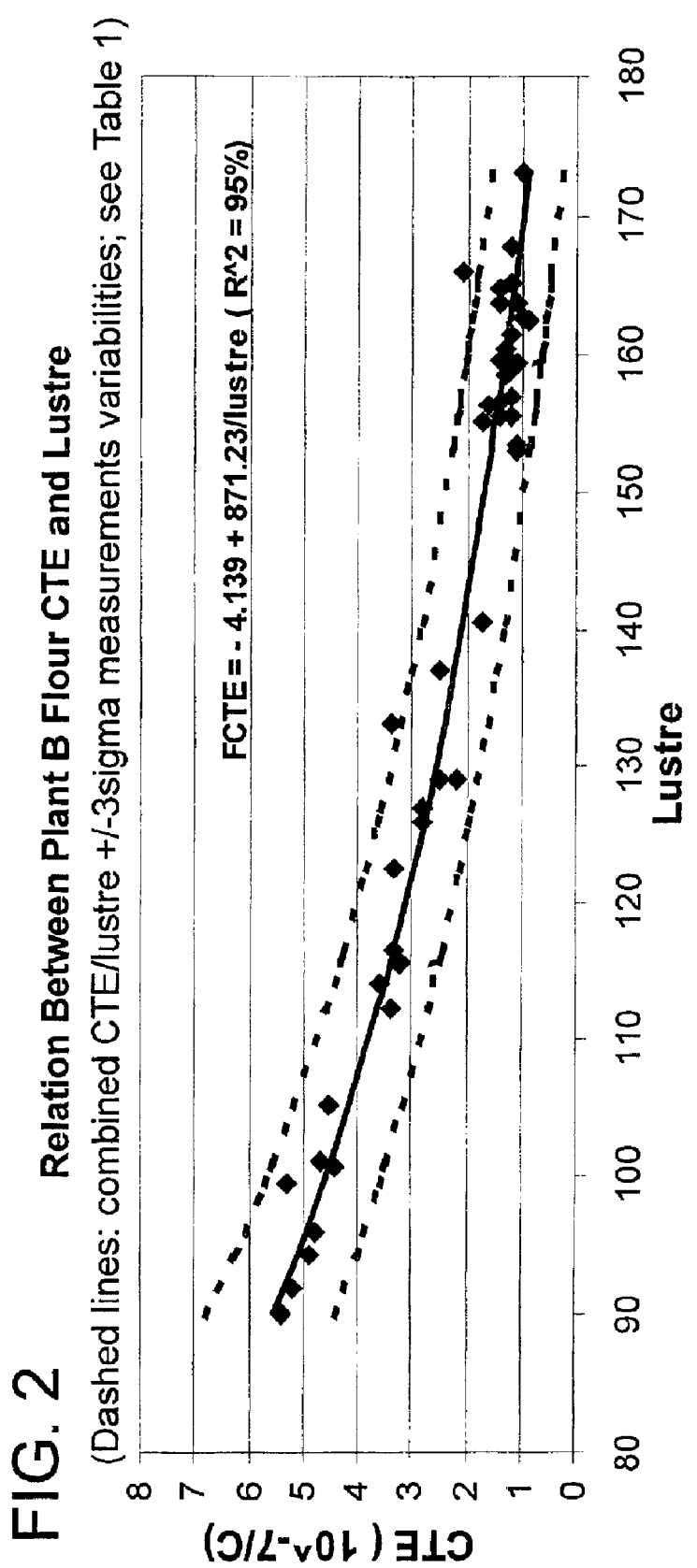
FIG. 2 is a graph depicting relation between Plant B cokes flour CTE and lustre.

The simple regressions (maximum $R^2$ criteria) shown in FIGS. 1 and 2 indicate excellent relations between plant generated CTEs and lustre given the combined lustre/CTE measurement variabilities. The dashed lines in FIGS. 1 and 2 were obtained by translation of the mean regression lines in the horizontal and vertical directions by the $\pm 3\sigma$ values (see Table 1) of the corresponding measurements.

Based on the above findings regarding the low variability of the lustre test as well as its excellent correlation with CTEs, it is believed that significant advantages will be achieved since the lustre test is relatively simple and fast. Therefore, it is cheaper to maintain and easier to control as compared with conventional CTE measurement processes based on baked and extruded artifacts.

The following procedures were employed in the foregoing example:

Sample Preparation Time required for one sample: 1.7 hours
1. Riffle sample to obtain a representative portion (~1000 g)
2. Sieve to remove natural 28/100 particles
3. De-oil (stays in oven ~24 hours)
4. Crush and sieve coke to obtain ~400 g of 28/100 Ty particles Sample Analysis Time required for one sample: 10 minutes
1. At beginning and end of each day, analyze the coke reference sample for SPC purposes.
2. Pour coke into sample tray and smooth surface.
3. Place sample tray under camera, activate program.
4. Computer automatically takes the average of 16 frames acquired consecutively.
5. Re-Pour and analyze sample five times.

Alternate Embodiment

Figure 5:
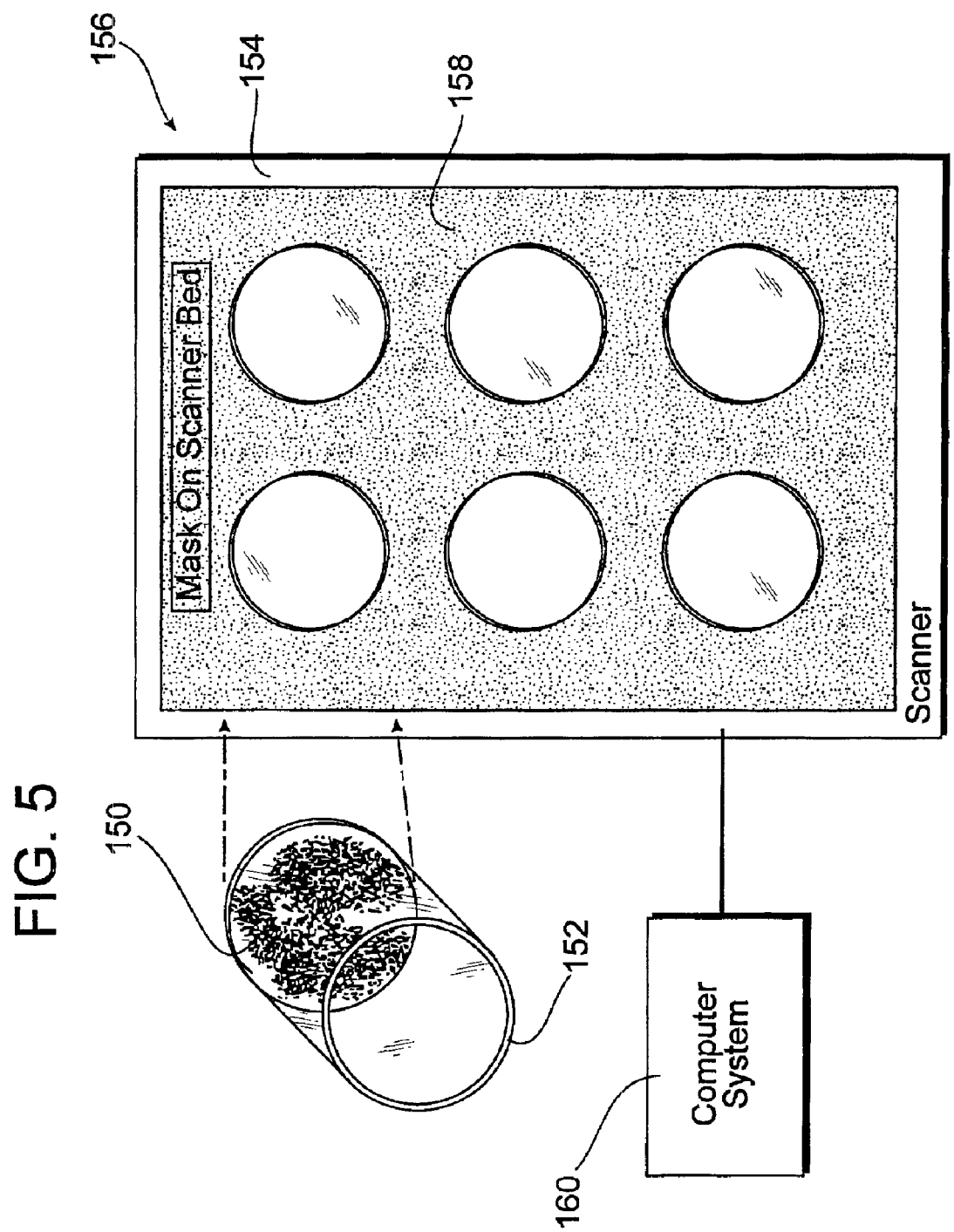
FIG. 5 is a schematic representation of an alternate embodiment utilizing the teachings of the present invention.

FIG. 5 shows an alternate embodiment utilizing a scanner to employ the teachings of the present invention. In the alternate embodiment, a number of steps are employed. An initial step is to obtain a representative sample from a petroleum product such as a coke.

The representative sample is then prepared in accordance with standard laboratory protocol such as sieving, deoiling, and such. The properly prepared sample 150 is then placed in a sample holder 152. The sample holder consists of an open-ended cylinder with a transparent end. The transparent end may be clear plastic or other material. While the sample holder 152 in the present embodiment is described as a cylinder, it will be understood that other forms may be utilized within the teachings of the present invention.

The sample 150 is poured into the open end of the holder 152 and then given a mild tap to settle the sample coke particles against the transparent end. The holder is thereafter placed on a glass plate 154 of a flat bed scanner 156. A mask 158 may be placed on the glass plate 154 of the scanner 156 with an opening or openings for the sample or samples.

The scanner 156 is a well known device capable of analyzing an image and processing it. Various types of scanners may be used within the teachings of the present invention although a flat bed scanner is preferred. The scanner 156 includes a CCD array which is a collection of tiny light sensitive diodes which convert light into electrons. A lamp in the scanner is used to illuminate the sample. The image of the sample 150 reaches the CCD array through a series of mirrors, filters and lenses. The various components are included in a scan head which is moved by a belt attached to a stepper motor.

The digital image produced by the scanner 156 is then quantified by measuring the gray levels present in the image. The gray levels are measured from 0 being the blackest to 255 being the whitest, and the data is then stored as a set of numbers. The highest gray levels are extracted to produce a representative lustre measurement for the sample. In the present case, the gray levels over a certain threshold number are selected and extracted. During the extraction and the filtration process, a personal computer 160 having a central processing unit is preferably used although specialized equipment having pattern recognition digital processing functions may be alternately employed.

At least two different types of measurements may be made with the scanner 156. Initially, a lustre measurement may be made in relation to the method described above. In addition, the sample may be measured relative to a calibrated optical density scale and then correlated to the lustre measurement.

In the first type of measurement, a reference coke is placed on the scanner 156 and imaged in the same scan as the sample or samples of interest. Using the threshold procedure described above, the reference coke is thresholded to yield the reference lustre value. The threshold (the lower limit gray scale value through the highest gray scale value) determined for the reference coke is used to threshold the sample being examined and the lustre value is directly determined by measuring the percent area of the sample occupied by pixels falling into the referenced threshold range.

In the second type of measurement, calibrated optical density scales are used to create a calibration curve of optical density versus gray scale. The optical density scales are placed in front of the sample mass directly on the bed of the scanner and imaged with the sample being considered. The calibration curve of optical density versus gray scale is created for the calibrated optical density scale. The average gray scale for each sample is determined and converted to optical density, using the optical density versus gray scale calibration curve.

Table 2 illustrates the values received for the two types of measurements. Ten coke samples were used to obtain data. In the Scan 1 method, a single sample was used. In the Scan 2 method, the sample plus a monitor were scanned together. Finally, in the current method, a CCD camera was used as previously described.

Finally, the data from the two scanner methods and lustre test data were charted on a graph as shown in FIG. 6. The left side Y scale shows the Scan 1 value, the right side Y scale shows the Scan 2 value. The data from the CCD camera lustre is shown on the X-axis.

From the foregoing, it will be observed that each of the scanner methods correlates well with the CCD camera lustre data.

The present invention may be applied and utilized in the petroleum refining process as a quality evaluation for coke as a part of the refining process, including but not limited to, identifying the effect of product or feedstock changes on the suitability of petroleum coke for particular applications.

Additionally, while the foregoing has been specifically described with relation to coke, the teachings of the invention may be equally pertinent to other petroleum products in particle form.

Whereas, the present invention has been described in relation to the drawings attached hereto, it should be understood that other and further modifications, apart from those shown or suggested herein, may be made within the spirit and scope of this invention.

TABLE 1

Comparison of CTEs and Lustre Measurements Variabilities

| | Test | | | | | |
|---|---|---|---|---|---|---|
| | Flour GTE Monitor (950169) | | Coarse Grain GTE Monitor (950169) | | Lustre Monitor (980029) | |
| Lab | Mean | 3σ | Mean | 3σ | Mean | 3σ |
| Plant B | 1.60 | 0.45 | 4.11 | 0.55 | — | — |
| Plant A | 1.80 | 0.42 | 4.13 | 0.73 | — | — |
| Plant C | 2.12 | 0.55 | 4.38 | 0.32 | 180 | 6.9 |

Notes:

TABLE 2

| ID | Method | Lustre | Range |
|---|---|---|---|
| 950368 | Scan1 | 943 | 58 |
| 980013 | Scan1 | 911 | 15 |
| 980059 | Scan1 | 914 | 29 |
| 980152 | Scan1 | 1017 | 16 |
| 980188 | Scan1 | 969 | 24 |
| 980191 | Scan1 | 949 | 18 |
| 980243 | Scan1 | 975 | 32 |
| 980276 | Scan1 | 981 | 8 |
| 990274 | Scan1 | 943 | 13 |
| 000010 | Scan1 | 952 | 16 |
| 950368 | Scan2 | 170.2 | 12 |
| 980013 | Scan2 | 189.8 | 20 |
| 980059 | Scan2 | 194.8 | 12 |
| 980152 | Scan2 | 90.6 | 12 |
| 980188 | Scan2 | 137.6 | 10 |
| 980191 | Scan2 | 153.6 | 26 |
| 980243 | Scan2 | 137.8 | 16 |
| 980276 | Scan2 | 112.8 | 17 |
| 990274 | Scan2 | 180 | 19 |
| 000010 | Scan2 | 149.6 | 9 |
| 950368 | Current | 170 | 9 |
| 980013 | Current | 215 | 15 |
| 980059 | Current | 192 | 10 |
| 980152 | Current | 76 | 8 |
| 980188 | Current | 129 | 4 |
| 980191 | Current | 155 | 9 |
| 980243 | Current | 109 | 5 |
| 980276 | Current | 112 | 8 |
| 990274 | Current | 181 | 9 |
| 000010 | Current | 147 | 9 |

What is claimed is:

1. A method for testing a petroleum product produced during refining to classify said product, said method comprising the steps of:

a) obtaining and preparing a representative sample of said product;

b) forming a digital image of said sample with a scanner; and c) processing said digital image by extracting and filtering said digital image to produce a representative lustre measurement of said sample wherein said b) and c) are iterated a plurality of times and including the additional step of totaling said representative lustre measurement of said sample produced during each of said iterations and then averaging said total to obtain an average lustre measurement of said sample; and d) further including the step of comparing said average lustre measurement to established parameters to assign a coefficient of thermal expansion (CTE) value to said sample to determine the CTE of said product, given historical correlation between CTE and lustre measurements.

2. A method for testing as recited in claim 1 wherein said step b) of forming a digital image of said sample with a scanner includes the steps of placing said sample in a cylinder having a transparent end, placing said transparent end on a glass plate of said scanner, and blocking said plate.

3. A method of testing as recited in claim 1 further including the step of repeating all previous steps for successive samples and designating each sample as to low or high CTE.

4. A method of testing as recited in claim 1 further including the step of varying known operating parameters during petroleum refining to alter said lustre measurement of said sample in order to obtain a product with a desirable CTE.

5. A method for testing a petroleum product in particle form to classify said product, said method comprising the steps of:

(a) placing a sample of said particles next to a calibrated optical density scale on a a scanner;

(b) using said scanner to produce a visible reflection image of light from said sample particles and said optical density scale;

(c) creating a calibration curve of optical density versus gray scale using the optical density scale image; and (d) determining the average gray scale value of the sample image and converting it to optical density using said calibration curve.

6. A method for testing as recited in claim 5 wherein step (a) includes the steps of placing said sample of particles in a container having at least one transparent side, and placing said transparent side on said scanner next to said calibrated optical density scale.

7. A method as set forth in claim 5 including the additional step of repeating steps a) through d) a plurality of times to obtain an average lustre measurement.

8. A method for testing as set forth in claim 7 including the step of varying known operating parameters during petroleum refining to alter said lustre measurement of said sample in order to obtain a product with a desirable CTE.

9. A method as set forth in claim 5 including the additional step of comparing said optical density determined in step d) against established parameters.

* * * * *